US010555724B2

United States Patent
Wen et al.

(10) Patent No.: US 10,555,724 B2
(45) Date of Patent: Feb. 11, 2020

(54) ULTRASOUND PROBE CALIBRATION PHANTOM, ULTRASOUND PROBE CALIBRATION SYSTEM AND CALIBRATION METHOD THEREOF

(71) Applicant: SHENZHEN INSTITUTES OF ADVANCED TECHNOLOGY, CHINESE ACADEMY OF SCIENCES, Shenzhen (CN)

(72) Inventors: Tiexiang Wen, Shenzhen (CN); Jia Gu, Shenzhen (CN); Yaoqin Xie, Shenzhen (CN); Lei Wang, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 350 days.

(21) Appl. No.: 15/519,531

(22) PCT Filed: Dec. 31, 2015

(86) PCT No.: PCT/CN2015/100063
§ 371 (c)(1),
(2) Date: Apr. 14, 2017

(87) PCT Pub. No.: WO2017/036044
PCT Pub. Date: Mar. 9, 2017

(65) Prior Publication Data
US 2017/0245837 A1 Aug. 31, 2017

(30) Foreign Application Priority Data
Sep. 1, 2015 (CN) .......................... 2015 1 0551128

(51) Int. Cl.
*H04B 17/00* (2015.01)
*A61B 8/00* (2006.01)

(52) U.S. Cl.
CPC ............ *A61B 8/587* (2013.01); *A61B 8/4254* (2013.01); *A61B 8/4444* (2013.01)

(58) Field of Classification Search
None
See application file for complete search history.

(56) References Cited

U.S. PATENT DOCUMENTS

| 2006/0084859 A1* | 4/2006 | Johnson | A61B 5/0507 600/407 |
| 2006/0287596 A1* | 12/2006 | Johnson | A61B 5/4312 600/437 |

(Continued)

FOREIGN PATENT DOCUMENTS

| CN | 102319117 A | 1/2012 |
| CN | 104161546 A | 11/2014 |

(Continued)

OTHER PUBLICATIONS

International Search Report for PCT/CN2015/100063 dated May 30, 2016 and its English translation provided by WIPO.

(Continued)

*Primary Examiner* — Isam A Alsomiri
*Assistant Examiner* — Jonathan D Armstrong

(57) ABSTRACT

An ultrasound probe calibration system and method. The system comprises an ultrasound probe calibration phantom (100), and the ultrasound probe calibration phantom (100) is provided with a sunken recess (110) at a middle position of an upper surface thereof and with several conical holes on a side surface thereof. The sunken recess (110) is fixedly connected with a two dimensional ultrasound probe (220) therein. The conical hole is inserted with an NDI insertion stylus (230), and a tip of the NDI insertion stylus (230) can be acquired in ultrasound imaging. An ultrasound probe calibration system employing the above structure enables a midplane of an ultrasound plane to pass a midplane of an ultrasound probe calibration phantom (100) along a middle gap, such that a tip of an NDI insertion stylus (230) is used for the midplane of the ultrasound plane, thereby addressing (Continued)

the problem of misalignment of a point-type phantom or a two-dimensional plane-type phantom to the ultrasound plane.

2 Claims, 3 Drawing Sheets

(56) References Cited

U.S. PATENT DOCUMENTS

| | | | | |
|---|---|---|---|---|
| 2007/0156021 | A1* | 7/2007 | Morse | A61B 1/0019 600/167 |
| 2007/0282200 | A1* | 12/2007 | Johnson | A61B 5/05 600/437 |
| 2008/0146932 | A1* | 6/2008 | Chalana | A61B 5/204 600/447 |
| 2012/0057428 | A1* | 3/2012 | Specht | A61B 8/00 367/13 |
| 2014/0043933 | A1* | 2/2014 | Belevich | A61B 8/587 367/11 |
| 2014/0275966 | A1* | 9/2014 | Schwartz | A61B 8/4236 600/411 |
| 2015/0224346 | A1* | 8/2015 | Coviello | G01S 7/52047 600/439 |
| 2018/0000444 | A1* | 1/2018 | Dayton | A61B 8/0883 |

FOREIGN PATENT DOCUMENTS

| | | |
|---|---|---|
| CN | 104207801 A | 12/2014 |
| CN | 105193445 A | 12/2015 |
| JP | 2005152187 A | 6/2005 |
| WO | 2015092664 A2 | 6/2015 |

OTHER PUBLICATIONS

Written Opinion of the International Search Authority for PCT/CN2015/100063 dated May 30, 2016 and its English translation provided by WIPO.

* cited by examiner

A

ULTRASOUND PROBE CALIBRATION PHANTOM, ULTRASOUND PROBE CALIBRATION SYSTEM AND CALIBRATION METHOD THEREOF

CROSS REFERENCE TO RELATED APPLICATIONS

The present application is the U.S. national phase of PCT Application PCT/CN2015/100063 filed on Dec. 31, 2015, which claims to the Chinese patent application No. 201510551128.1 filed on Sep. 1, 2015, the disclosures of which are incorporated herein by reference in their entireties.

TECHNICAL FIELD

The invention relates to the technical field of ultrasonic images, in particular to a calibration phantom and system of an ultrasonic probe and a method of calibration thereof.

BACKGROUND ART

Ultrasonic imaging has been widely used in ultrasonic image guided interventional operation and reestablishment of three-dimensional volume data. However, a common two-dimensional ultrasonic probe does not have peripheral positioning equipment, so ultrasonic image data cannot be directly used in operation. Therefore, a corresponding transformation relation must be established between a locating device and an ultrasonic imaging plane. Calibration of an ultrasonic probe is a process of confirming the transformation relation of transforming a coordinate system of a position sensor fixed on the ultrasonic probe into a coordinate system of a two-dimensional ultrasonic imaging plane.

In a calibration algorithm of the ultrasonic probe, design and making of calibration model are crucial. The quality of the design of the model directly affects complexity of calibration operation, clearness of imaging of calibration feature points, convenience of extraction of the feature points and precision of follow-up calibration solving. Typical calibration models for ultrasonic probes can be divided into the following two kinds: phantom-based calibration models and stylus-based calibration models.

In single-point phantom calibration, a round object (as shown in FIG. 1a) or an intersection point of intersection lines (as shown in FIG. 1b) are scanned and imaged at multiple angles, and the object is separated from a scanned image, and is generally regarded as the origin of coordinates of a phantom object for solving. Calibration precision of the kind of method depends on locating accuracy to an object of a feature point on an ultrasonic image, and the ultrasonic image plane requires exactly passing through the center point of the object of the feature point. Several intersection lines form several imagable round intersection points in the multi-point and intersection line phantom, which also requires the ultrasonic image plane to pass through the plane with the intersection points. The several intersection points often have a three-point collinear or three-point coplanar triangular relation (as shown in FIG. 1c), and a calibration equation is solved by utilizing such geometrical-restriction relation. Calibration thinking of a two-dimensional-shaped phantom is similar to that of a multi-point phantom, which scans the intersection points (as shown in FIG. 1d) of the intersection lines instead of the geometric angular points of a two-dimensional planar object, and generally shows higher brightness value in terms of the scanned images. A three-intersection-line phantom consists of three intersection lines which are perpendicular in a pairwise manner (as shown in FIG. 1e). As the original intention of the design of the phantom, a coordinate system consisting of the three intersection lines is used as a local coordinate system of the phantom, so that an ultrasonic scanning plane is unnecessarily to be perpendicular to a calibration phantom of an ultrasonic probe, and can simplify scanning operation relatively.

As the method of calibration of a surface phantom, a flat plate capable of imaging clearly in ultrasound is fixed at the bottom of a water tank or in the water tank and is used as the calibration phantom of the ultrasonic probe; the image of the phantom in ultrasound is a straight line, so that follow-up image features (straight line) are easier to be extracted, and the quantity of points on the straight line can be quite rich for the solving of the calibration equation. N-shaped targets (as shown in FIG. 1f) are formed by an N-shaped phantom through a layer or multiple layers of nylon wires; when an ultrasonic plane passes through the N-shaped targets, each N-shaped target wire produces three bright spot feature points on the image. After coordinates of three bright spots of each N-shaped target wire are manually recognized and picked up, a three-dimensional coordinate value of an intersection point of the corresponding N-shaped target and the imaging plane in a design coordinate system can be solved as per the ratio of the distance between the left bright spot and the middle bright spot to the distance between the right bright spot and the middle bright spot according to the design constraint of the model.

In recent years, because N-shaped phantoms are simple to be made and speedy and convenient to be scanned, they have been widely used. However, a sound field of an ultrasonic probe is diffused with increase of scanning depth; and the ultrasonic imaging plane is not an ideal geometric plane. An imaging plane with certain thickness is intersected with a linear target; projection of a transmitting target on an ideal imaging plane cannot be comparable to a point, thus, a linear and even arc-shaped bright spot feature point is formed. However, the light spot has quite large error and uncertainty when the coordinates of a mark point are manually or automatically picked up, which results in larger error in calculation of reestablishment of three-dimensional coordinates of the N-shaped targets, loss of co-planarity which originally existed in the process, and reduction of calibration precision.

SUMMARY

Based on these above, the invention provides a calibration phantom of an ultrasonic probe to effectively solve problems existing in the prior art.

On one hand, the invention provides a calibration phantom of an ultrasonic probe; a concave groove is formed in the middle of the upper surface of the calibration phantom of the ultrasonic probe; and several conical holes are formed on a side surface of the calibration phantom of the ultrasonic probe.

On the other hand, the invention further provides a calibration system of an ultrasonic probe, comprising:
an ultrasonic water tank, which contains purified water;
a calibration phantom of an ultrasonic probe, which is fixed in the ultrasonic water tank, wherein the purified water exactly submerges the calibration phantom of the ultrasonic probe; a concave groove is formed in the middle of the upper surface of the calibration phantom of the ultrasonic probe;

and a plurality of conical holes are formed on a side surface of the calibration phantom of the ultrasonic probe;

a two-dimensional ultrasonic probe, which is fixed in the concave groove, wherein a locating and tracking device is further fixed in the two-dimensional ultrasonic probe; and NDI puncture probes, which are inserted in the conical holes, so that tips of the NDI puncture probes are acquired through ultrasonic images.

In some embodiments, the calibration phantom of the ultrasonic probe is made of a material with good ultrasonic wave permeability.

In some embodiments, the calibration phantom of the ultrasonic probe is made of organic glass.

In another aspect, the invention further provides a method of calibration of an ultrasonic probe, comprising the following steps:

fixing the calibration phantom of the ultrasonic probe in the ultrasonic water tank, and enabling the purified water in the ultrasonic water tank to exactly submerge the calibration phantom of the ultrasonic probe, wherein the concave groove is formed in the middle of the upper surface of the calibration phantom of the ultrasonic probe, and the conical holes are formed on the side surface of the calibration phantom of the ultrasonic probe;

fixing the two-dimensional ultrasonic probe in the concave groove, and further fixing the locating and tracking device in the two-dimensional ultrasonic probe;

inserting the NDI puncture probes in the conical holes, and acquiring tips of the NID puncture probes through ultrasonic images;

simultaneously acquiring position information of the tips and position information of the locating and tracking device in a world coordinate system through the NDI puncture probes, and respectively marking the position information of the tips and the position information of the locating and tracking device as $y_i$ and $T_{S \to W}$;

recording the pixel position information of the tips on the ultrasonic image plane, and marking the pixel position information as $x_i$, wherein $y_i = T_{S \to W} \cdot T_{P \to S}$ and $T_{P \to S}$ is a transformation matrix of an unknown ultrasonic imaging plane coordinate system P to an ultrasonic probe locating device coordinate system S; and solving the transformation matrix $T_{P \to S}$ by an image registration algorithm based on an iterative closest point to synchronously acquire space calibration and time calibration.

In some embodiments, the method further comprises the following steps:

changing the positions of the NDI puncture probes in the calibration phantom of the ultrasonic probe, acquiring a point set pair of positions of the tips in some lines, and marking the point set pair as $Y=\{y_i, i \in m\}$ and $X=\{x_i, i \in n\}$, where m is not equal to n, and m and n are natural numbers; and establishing the following formula according to the image registration algorithm based on the iterative closest point, wherein a process of iteratively solving the following formula can be regarded as a process of iteratively minimizing the following two equations:

$$c_i^k = \underset{y_i \in Y}{\operatorname{argmin}} \sum_{i=1}^{m} |T^k(x_i) - y_i|^2, \quad T^{k+1} = \underset{T}{\operatorname{argmin}} \sum_{i=1}^{n} |T(x_i) - c_i^k|^2;$$

transforming every point $ix \in X$ of a set X by a current transformation matrix T k, finding a point which is the closest to $T^k(x_i)$ in a set Y, and marking the point as a corresponding point $c_i^k$ of $k^{th}$ iteration, wherein the result of the step is a set $(x_i, c_i^k)$ of a corresponding point pair; and repeating the operation, and finding a transformation matrix T to enable a point set $Y=\{y_i, i \in m\}$ and a point set $X=\{x_i, i \in n\}$ to be aligned with each other.

In some embodiments, the calibration phantom of the ultrasonic probe is made of the material with good ultrasonic wave permeability.

In some embodiments, the calibration phantom of the ultrasonic probe is made of the organic glass.

By the technical solution, the invention has the following beneficial effects:

As for the calibration phantom of the ultrasonic probe provided by the invention, the concave groove is formed in the middle of the upper surface of the calibration phantom of the ultrasonic probe; the conical holes are formed on the side surface of the calibration phantom of the ultrasonic probe; owing to the structure of the calibration phantom of the ultrasonic probe, the two-dimensional ultrasonic probe can be fixed on the calibration phantom of the ultrasonic probe, which avoids accidental shake errors caused by manually grasping the two-dimensional ultrasonic probe and the like, and greatly improves the practicability of the calibration system.

As for the calibration system of the ultrasonic probe provided by the invention, the concave groove is formed in the middle of the upper surface of the calibration phantom of the ultrasonic probe; the conical holes are formed on the side surface of the calibration phantom of the ultrasonic probe; the inside of the concave groove is fixedly connected with the two-dimensional ultrasonic probe; the NDI puncture probes are inserted in the conical holes; the tips of the NDI puncture probes can be acquired by the ultrasonic images; the calibration system of the ultrasonic probe with the structure is used; a neutral surface of an ultrasonic plane can exactly pass through a neutral surface of the calibration phantom of the ultrasonic probe along a gap in the middle, so that the neutral surface of the ultrasonic plane exactly adopts the tips of the NDI puncture probes; and therefore, the problem that a 'point-shaped' phantom and a two-dimensional 'surface-shaped' phantom cannot be aligned with the ultrasonic plane is solved well; and As for the method of calibration of the ultrasonic probe provided by the invention, the image registration algorithm based on the iterative closest point is adopted, so that (i) a corresponding relation between two point sets (feature points on the calibration phantom of the ultrasonic probe and corresponding feature points on the ultrasonic imaging plane) can be found out automatically, and synchronization of the two point sets on time is not required; (ii) the set numbers of the two point sets are not required to be equal; and (iii) once the transformation matrix is solved and obtained, delayed time between image data and locating data in the calibration system can be solved reversely, and therefore, the problem of space calibration and time calibration of the ultrasonic probe can be solved well by the algorithm.

BRIEF DESCRIPTION OF THE DRAWINGS

in FIG. 1, (b) is a structure diagram of a single-intersection-line phantom of a calibration phantom of an ultrasonic probe provided in the prior art;

in FIG. 1, (c) is a structure diagram of a multi-intersection-line phantom of a calibration phantom of an ultrasonic probe provided in the prior art;

in FIG. 1, (d) is a structure diagram of a two-dimensional-shaped phantom of a calibration phantom of an ultrasonic probe provided in the prior art;

in FIG. 1, (e) is a structure diagram of a three-intersection-line phantom of a calibration phantom of an ultrasonic probe provided in the prior art;

in FIG. 1, (f) is a structure diagram of an N-shaped phantom of a calibration phantom of an ultrasonic probe provided in the prior art;

DETAILED DESCRIPTION

Figure 1:
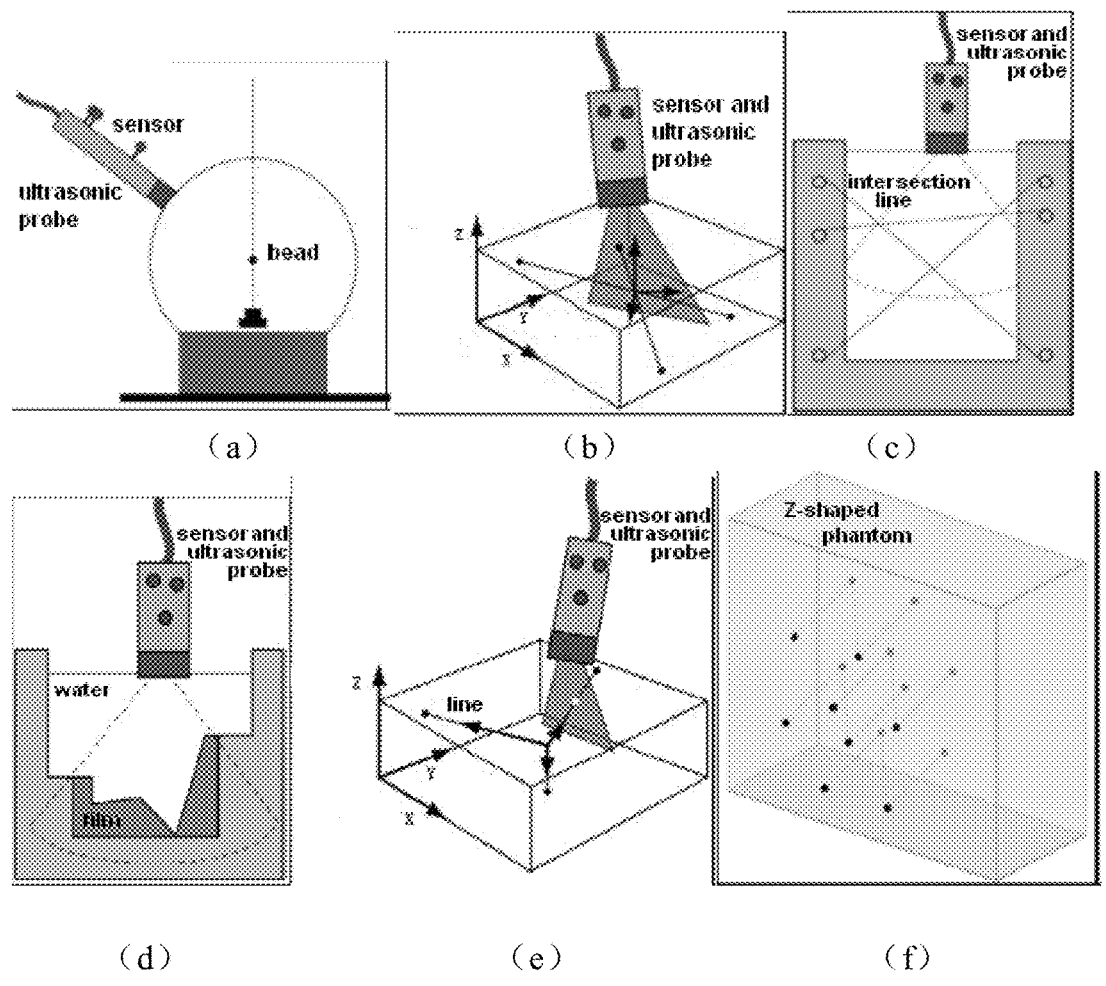
In FIG. 1, (a) is a structure diagram of a point phantom of a calibration phantom of an ultrasonic probe provided in the prior art.

For understanding the invention conveniently, the invention will be described more comprehensively below with reference to the related drawings.

In the drawings, preferred embodiments of the invention are shown. The above description is only the preferred embodiments of the invention and does not limit the scope of the patent of invention; any equivalent structure or equivalent process modification used according to the contents of the specification and drawings in the invention, no matter whether it is directly or indirectly used in any other related technical fields, should be included within the protection scope of the patent of invention.

Figure 2:
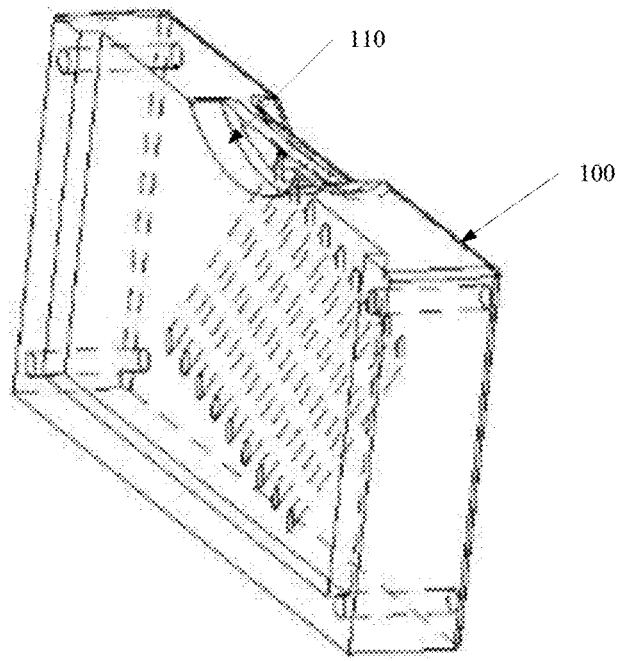
FIG. 2 is a structure diagram of a calibration phantom of an ultrasonic probe provided by an embodiment of the invention.

As shown in FIG. 2, an embodiment of the invention provides a calibration phantom 100 of an ultrasonic probe; a concave groove 110 is formed in the middle of the upper surface of the calibration phantom 100 of the ultrasonic probe; and a plurality of conical holes (not shown) are formed on the side surface of the calibration phantom 100 of the ultrasonic probe.

It may be appreciated that the calibration phantom 100 of the ultrasonic probe is made of a material with good ultrasonic wave permeability, and particularly, the calibration phantom 100 of the ultrasonic probe is made of organic glass.

As for the calibration phantom 100 of the ultrasonic probe provided by the invention, because the concave groove 110 is formed in the middle of the upper surface, several conical holes are formed on the side surface; because such structure of the calibration phantom of the ultrasonic probe makes the two-dimensional ultrasonic probe able to be fixed on the calibration phantom of the ultrasonic probe, accidental shake errors caused by the reason that the two-dimensional ultrasonic probe is grasped manually and the like are avoided, which greatly improves the practicability of the calibration system.

Figure 3:
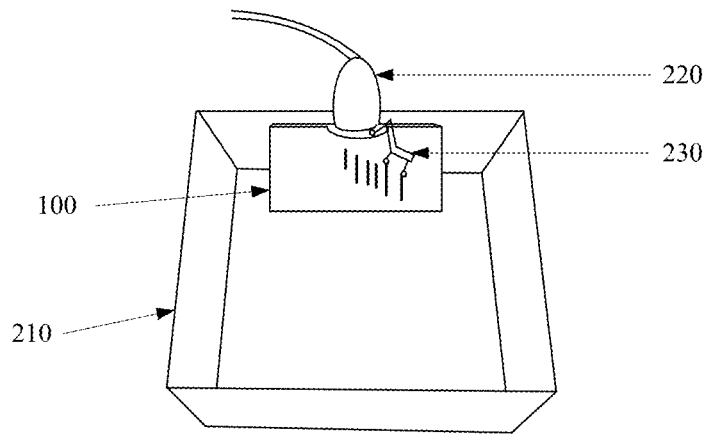
FIG. 3 is a structure diagram of a calibration system of an ultrasonic probe provided by an embodiment of the invention.

As shown in FIG. 3, an embodiment of the invention provides a calibration system of an ultrasonic probe, which comprises an ultrasonic water tank 210, a calibration phantom 100 of an ultrasonic probe, a two-dimensional ultrasonic probe 220 and NDI puncture probes 230.

Wherein, the ultrasonic water tank 210 contains purified water; the calibration phantom 100 of the ultrasonic probe is fixed in the ultrasonic water tank 210; the purified water exactly submerges the calibration phantom 100 of the ultrasonic probe; the two-dimensional ultrasonic probe 220 is fixed in the concave groove 110; a locating and tracking device (not shown) is further fixed in the two-dimensional ultrasonic probe 220; the NDI puncture probes 230 are fixedly inserted in the conical holes; and tips of the NDI puncture probes 230 can be acquired through ultrasonic images.

The calibration system 200 of the ultrasonic probe adopting the above structure in the invention can make the neutral surface of an ultrasonic plane exactly pass through a neutral surface of the calibration phantom of the ultrasonic probe along a gap in the middle, so that the neutral surface of the ultrasonic plane exactly adopts the tips of the NDI puncture probes, and therefore, the problem that a 'point-shaped' phantom and a two-dimensional 'surface-shaped' phantom cannot be aligned with the ultrasonic plane is solved well.

Figure 4:
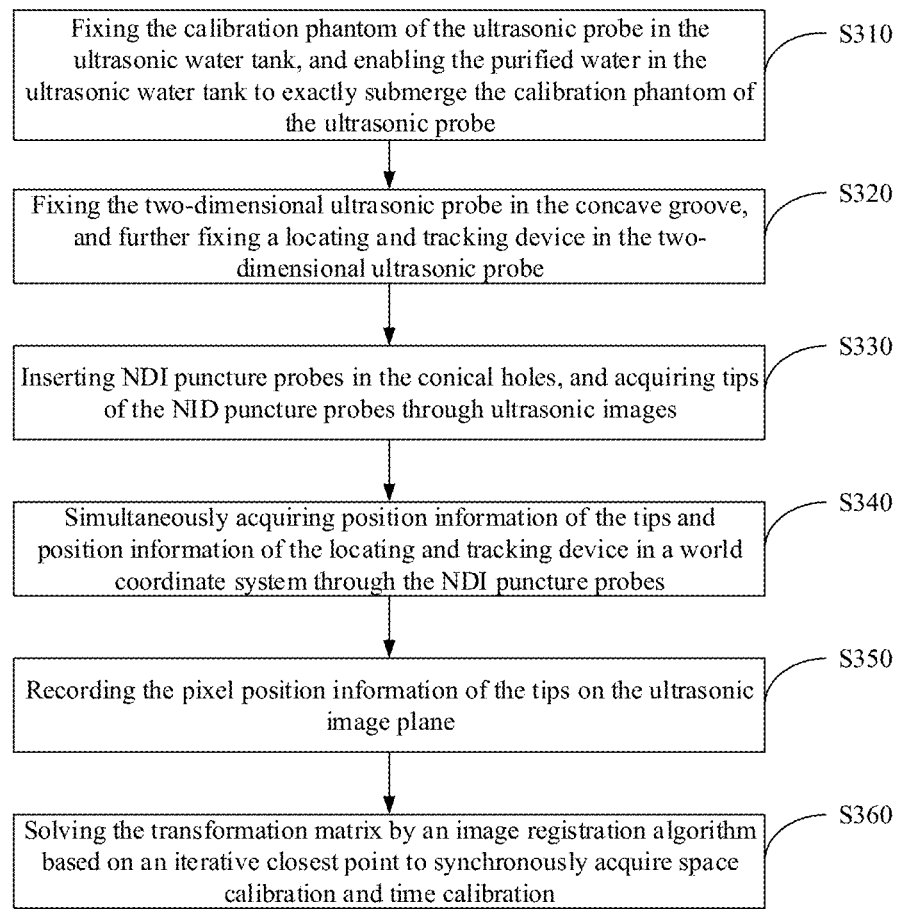
FIG. 4 is a flow diagram of steps of a method of calibration of an ultrasonic probe provided by an embodiment of the invention.
Figure 5:
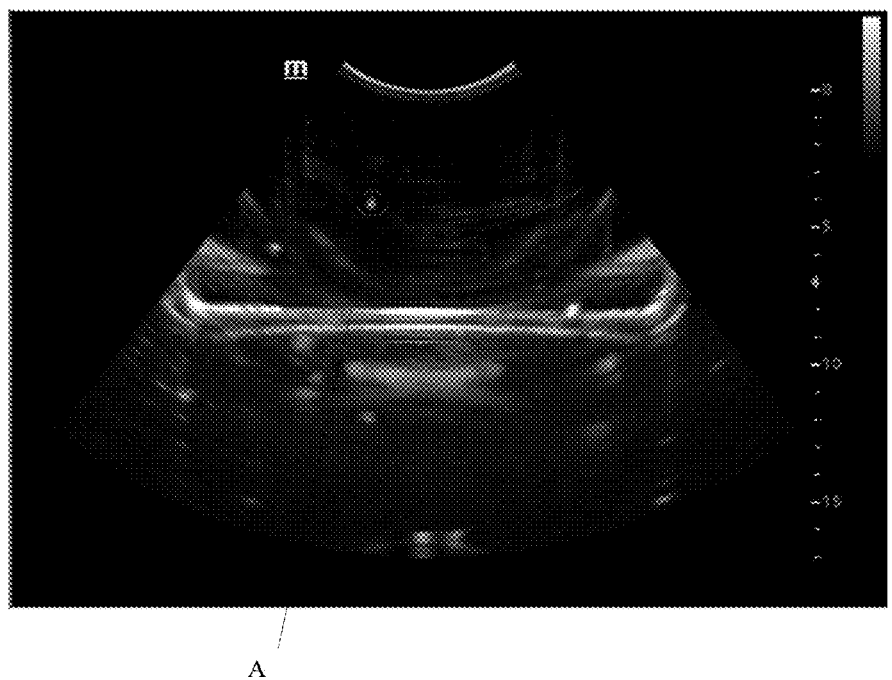
FIG. 5 is an image of NDI puncture probes provided by an embodiment of the invention on an ultrasonic probe.

As shown in FIG. 4, the flow diagram of steps of a method of calibration of an ultrasonic probe provided in the embodiment of the invention comprises the following steps:

step S310: fixing the calibration phantom of the ultrasonic probe in the ultrasonic water tank, and enabling the purified water in the ultrasonic water tank to exactly submerge the calibration phantom of the ultrasonic probe;

step S320: fixing the two-dimensional ultrasonic probe in the concave groove, and further fixing a locating and tracking device in the two-dimensional ultrasonic probe;

step S330: inserting the NDI puncture probes in the conical holes, and acquiring the tips of the NDI puncture probes through the ultrasonic images, wherein it may be appreciated that an acquired tip image should be a point of intersection between another side wall in a gap and an ultrasonic plane theoretically, but because the actual ultrasonic plane has certain thickness, a quite small error exists, a dot A in a ring as shown in FIG. 5 can be obtained, an imaging effect shows that the imaging quality of feature points of the tips of the NDI puncture probes is excellent, and requirements of precision of manual and automatic separation can be met;

step S340: simultaneously acquiring position information of the tips and position information of the locating and tracking device in a world coordinate system through the NDI puncture probes, and respectively marking the position information of the tips and the position information of the locating and tracking device as $y_i$ and $T_{S \to W}$;

step S350: recording the pixel position information of the tips on the ultrasonic image plane, and marking the pixel position information as $x_i$, wherein $y_i = T_{S \to W} \cdot T_{P \to S} \cdot x_i$, $T_{P \to S}$ is a transformation matrix from an unknown ultrasonic imaging plane coordinate system P to an ultrasonic probe locating device coordinate system S; and it may be appreciated that $x_i$ and $y_i$ are different expressions of the same point in two different coordinate systems in space; and step S360: solving the transformation matrix $T_{P \to S}$ by the image registration algorithm based on the iterative closest point to synchronously acquire space calibration and time calibration.

It may be appreciated that the image registration algorithm based on the iterative closest point is used for solving a transformation matrix to be solved, which can simultaneously solve space calibration and time calibration, and greatly improve the precision of calibration.

Another embodiment further comprises the following steps:

step S370: changing the positions of the NDI puncture probes in the calibration phantom of the ultrasonic probe, acquiring a point set pair of positions of tips in some lines, and marking the point set pair as Y={$y_i$,i∈m} and X={$x_i$, i∈n}, where m is not equal to n, and m and n are natural numbers;

step S380: establishing the following formula according to the image registration algorithm based on the iterative closest point, wherein a process of iteratively solving the following formula can be regarded as a process of iteratively minimizing the following two equations:

$$c_i^k = \underset{y_i \in Y}{\mathrm{argmin}} \sum_{i=1}^m |T^k(x_i) - y_i|^2, \; T^{k+1} = \underset{T}{\mathrm{argmin}} \sum_{i=1}^n |T(x_i) - c_i^k|^2;$$

It may be appreciated that the most outstanding feature of the ICP algorithm is as follows: points in the point set X are not required to be in one-to-one correspondence to points in the point set Y completely. On the contrary, if the transformation matrix T corresponding to the two point sets are known, the one-to-one corresponding relation between the two point sets can be confirmed by ICP. In mathematics, the solving process of the ICP algorithm can be regarded as the process of iteratively minimizing the above two equations.

Step S390: transforming every point $x_i$∈X of the set X by a current transformation matrix $T^k$, finding a point which is the closest to $T^k(x_i)$ in the set Y, and marking the point as a corresponding point $c_i^k$ of $k^{th}$ iteration, wherein the result of the step is a set ($x_i$,$c_i^k$) of a corresponding point pair;

step S410: repeating the operation, and finding a transformation matrix T to enable a point set Y={$y_i$, i∈m} and a point set X={$x_i$, i∈n} to be aligned with each other.

The method of calibration of the ultrasonic probe provided by the invention adopts the image registration algorithm based on the iterative closest point, so that (i) a corresponding relation between two point sets (feature points on the calibration phantom of the ultrasonic probe and corresponding feature points on the ultrasonic imaging plane) can be found out automatically, and synchronization of the two point sets on time is not required; (ii) the set numbers of the two point sets are not required to be equal; and (iii) once the transformation matrix is solved and obtained, delayed time between image data and locating data in the calibration system can be solved reversely, and therefore, the problem of space calibration and time calibration of the ultrasonic probe can be solved well by the algorithm.

The above embodiments only express several embodiments of the invention, whose description is relatively specific and detailed, but it should not be construed as limiting the scope of the patent of invention. It should be noted that for those ordinary skilled in the art, various changes and modifications can further be carried out on the premise of not departing from the concept of the invention, and belong to the protection scope of the invention. Therefore, the protection scope of the patent of invention should be determined by the appended claims.

The invention claimed is:

1. A method of calibration of an ultrasonic probe, comprising following steps:

fixing a calibration phantom of the ultrasonic probe in a ultrasonic water tank, and enabling purified water in the ultrasonic water tank to exactly submerge the calibration phantom of the ultrasonic probe, wherein a concave groove is formed in the middle of the upper surface of the calibration phantom of the ultrasonic probe; and a plurality of conical holes are formed on the side surface of the calibration phantom of the ultrasonic probe;

fixing a two-dimensional ultrasonic probe in the concave groove, and further fixing a locating and tracking device in the two-dimensional ultrasonic probe;

inserting puncture probes in the conical holes, and acquiring tips of the puncture probes through ultrasonic images;

simultaneously acquiring position information of the tips and position information of the locating and tracking device in a world coordinate system through the puncture probes, and respectively marking the position information of the tips and the position information of the locating and tracking device as $y_i$ and $T_{S \to W}$;

recording the pixel position information of the tips on the ultrasonic image plane, and marking the pixel position information as $x_i$, wherein $y_i = T_{S \to W} \cdot T_{P \to S} \cdot x_i$, and $T_{P \to S}$ is a transformation matrix from an unknown ultrasonic imaging plane coordinate system P to an ultrasonic probe locating device coordinate system S; and solving the transformation matrix $T_{P \to S}$ by an image registration algorithm based on an iterative closest point to synchronously acquire space calibration and time calibration;

wherein, the method further comprises following steps:

changing the positions of the puncture probes in the calibration phantom of the ultrasonic probe, acquiring a point set pair of positions of at least six tips, and marking the point set pair as Y={$y_i$, i∈m} and X={$x_i$, i∈n}, where m is not equal to n, and m and n are natural numbers; and solving an optimal transformation matrix T to enable the point set pair Y={$y_i$, i∈m} and X={$x_i$, i∈n} to be aligned with each other;

wherein, solving the optimal transformation matrix T to enable the point set pair Y={$y_i$, i∈m} and X={$x_i$, i∈n} to be aligned with each other comprises:

step 1: transforming every point $x_i$ ∈X of a set X by using a formula (1) through a transformation matrix $T^k$, finding a point which is the closest to $T^k(x_i)$ in a set Y, and marking the point as a corresponding point $c_i^k$ of $k^{th}$ iteration to obtain a set ($x_i$, $c_i^k$) of a corresponding point pair, wherein the formula (1) is as follows:

$$c_i^k = \underset{y_i \in Y}{\mathrm{argmin}} \sum_{i=1}^m |T^k(x_i) - y_i|^2;$$

and step 2: solving a transformation matrix T according to a set ($x_i$, $c_i^k$) by using a formula (2) to obtain a direct transformation relation of a description point set pair Y={$y_i$, i∈m} and X={$x_i$, i∈n} wherein the formula (2) is as follows:

$$T^{k+1} = \underset{T}{\mathrm{argmin}} \sum_{i=1}^n |T(x_i) - c_i^k|^2;$$

and iteratively carrying out step 1 and step 2, and solving to obtain an optimal transformation matrix T to enable the point set pair Y={$y_i$, i∈m} and X={$x_i$, i∈n} to be aligned with each other.

2. The method of calibration of an ultrasonic probe of claim 1, wherein the calibration phantom of the ultrasonic probe is made of organic glass.

* * * * *